(12) United States Patent
Gössmann et al.

(10) Patent No.: US 10,525,183 B2
(45) Date of Patent: Jan. 7, 2020

(54) CHECK VALVE ASSEMBLY, MEDICAL FUNCTIONAL DEVICE AND A BLOOD TREATMENT APPARATUS

(71) Applicant: FRESENIUS MEDICAL CARE DEUTSCHLAND GMBH, Bad Homburg (DE)

(72) Inventors: Stephan Gössmann, Frankfurt am Main (DE); Jürgen Häcker, Neu-Anspach (DE); Ralf Müller, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 439 days.

(21) Appl. No.: 15/126,264

(22) PCT Filed: Mar. 13, 2015

(86) PCT No.: PCT/EP2015/055278
§ 371 (c)(1),
(2) Date: Sep. 14, 2016

(87) PCT Pub. No.: WO2015/136067
PCT Pub. Date: Sep. 17, 2015

(65) Prior Publication Data
US 2017/0080139 A1    Mar. 23, 2017

(30) Foreign Application Priority Data
Mar. 14, 2014    (DE) .................. 10 2014 103 489

(51) Int. Cl.
*A61M 1/16*        (2006.01)
*A61M 39/24*      (2006.01)
(Continued)

(52) U.S. Cl.
CPC ............ *A61M 1/169* (2013.01); *A61M 39/24* (2013.01); *F16K 15/18* (2013.01); *A61M 1/14* (2013.01);
(Continued)

(58) Field of Classification Search
CPC .......... A61M 1/169; A61M 2039/2493; A61M 39/24; F16K 15/18
See application file for complete search history.

(56) References Cited

U.S. PATENT DOCUMENTS 4,534,542 A    8/1985  Russo
4,967,791 A *  11/1990 Sternberger ............ F16K 15/18
                                                   137/522

(Continued)

FOREIGN PATENT DOCUMENTS

CN    102458505    5/2012
DE    3417686      11/1985
(Continued)

OTHER PUBLICATIONS

International Search Report from PCT/EP2015/055278, dated May 20, 2015.
(Continued)

*Primary Examiner* — Ariana Zimbouski
(74) *Attorney, Agent, or Firm* — Fish & Richardson P.C.

(57) ABSTRACT

A check valve assembly having an inlet and an outlet for medical fluids, comprising a valve body, wherein the check valve assembly in an initial state allows a flow of a working fluid and/or a sterilization fluid through the check valve assembly in both directions of flow, that is from the inlet to the outlet and vice versa, and wherein the check valve assembly in an operating state allows only one direction of flow of the working fluid, wherein the check valve assembly comprises a pin-pin-reception connection, which is embod-
(Continued)

ied so that the check valve assembly can be transferred from the initial state into the operating state by applying force on the pin-pin-reception connection and/or by an impression of path on the pin-pin-reception connection.

17 Claims, 3 Drawing Sheets

(51) Int. Cl.
 *F16K 15/18* (2006.01)
 *A61M 1/14* (2006.01)
(52) U.S. Cl.
 CPC .............. *A61M 2039/242* (2013.01); *A61M 2039/2453* (2013.01); *A61M 2039/2466* (2013.01); *A61M 2039/2486* (2013.01); *A61M 2039/2493* (2013.01); *A61M 2205/128* (2013.01)

(56) References Cited

U.S. PATENT DOCUMENTS

| | | |
|---|---|---|
| 5,954,313 A | 9/1999 | Ryan |
| 6,000,417 A * | 12/1999 | Jacobs ................ F16K 15/023 137/2 |
| 2002/0189684 A1 | 12/2002 | Williamson et al. |
| 2003/0140966 A1 * | 7/2003 | Kempf ................ E03B 7/045 137/337 |
| 2009/0140191 A1 | 6/2009 | Spliethoff et al. |
| 2010/0274169 A1 | 10/2010 | Lauer |
| 2010/0298782 A1 * | 11/2010 | Winsor ................ A61M 39/26 604/247 |

FOREIGN PATENT DOCUMENTS

| | | |
|---|---|---|
| DE | 20318192 | 2/2004 |
| DE | 102007058251 | 6/2009 |
| DE | 10 2009 024469 A1 | 1/2011 |
| WO | 2010-102784 A1 | 9/2010 |
| WO | WO 2010/102784 | 9/2010 |

OTHER PUBLICATIONS

International Preliminary Report on Patentability in Application No. PCT/EP2015/055278, dated Sep. 14, 2016, 11 pages.

* cited by examiner

CHECK VALVE ASSEMBLY, MEDICAL FUNCTIONAL DEVICE AND A BLOOD TREATMENT APPARATUS

CROSS REFERENCE TO RELATED APPLICATIONS

The present application is the national state entry of International Patent Application No. PCT/EP2015/055278, filed on Mar. 13, 2015, the disclosure of which is expressly incorporated herein in its entirety by reference thereto, and claims priority to Application No. DE 10 2014 103 489.9, filed in the Federal Republic of Germany on Mar. 14, 2014.

TECHNICAL FIELD

Aspects of the present invention relate to a check valve assembly, a medical functional device, and a blood treatment apparatus.

SUMMARY

Certain aspects of the present invention relate to a check valve assembly. In addition, suitable functional devices and blood treatment apparatuses are to be provided.

In some aspects, a check valve assembly has an inlet and an outlet for medical fluids, in particular, a working fluid, which comprises a valve body. The check valve assembly allows in an initial state a working fluid and/or a sterilization fluid to flow through the check valve assembly in both flow directions, that is from the inlet to the outlet, and vice versa. Further, the check valve assembly in an operating state allows only one flow direction of the working fluid, that is, from the inlet to the outlet.

The check valve assembly comprises a pin-pin-reception connection. This is embodied such that the check valve assembly can be transferred from the initial state into the operating state by applying a force on the pin-pin-reception connection or on the pin and/or by an impression of path on the pin-pin-reception connection or on the pin, preferably in the longitudinal direction of pin and pin-reception respectively.

The transfer can be effected by applying or by means of applying a force onto the pin-pin-reception connection, e.g. via the film in the initial state and by an effect or a force therethrough.

The medical functional device according to certain aspects of the present invention comprises at least one check valve assembly of the type described herein.

In some embodiments, the blood treatment apparatus, preferably embodied as a dialysis apparatus, comprises a receiving section for receiving a medical functional device of the type described herein.

The blood treatment comprises a movable limiting device, e.g. a door, for limiting the receiving section. The limiting device is embodied in a way such that through its movement one or all check valve assemblies received in the receiving section of the medical functional device is transferred from the initial state into the operating state.

In all of the following versions the use of the expression "may" or "may have", etc. is to be understood as a synonym to "is preferably" or "preferably has", etc. and it is to explain an exemplary embodiment according to the invention.

Whenever numerical words are mentioned herein, the skilled person understands this as an indication of a numerically lower limit. As long as it does not lead to any discernible contradiction for the skilled person, the skilled person, therefore, implicitly reads for example in the indication "one" at all times "at least one". This understanding is also encompassed by the present invention as well as the interpretation that, for example, "one" can alternatively be meant as "exactly one", as long as this is technically possible in the view of the skilled person. Both of which are encompassed by the present invention, and apply to all used numerical words herein.

Advantageous further developments of the present invention may be found in subject-matter of dependent claims and embodiments.

Exemplary embodiments may comprise one or more of the following stated features in any arbitrary combination.

In some exemplary embodiments, the pin-reception-pin-connection may be, or may comprise, the combination of a pin reception (or a pin-reception section) for receiving a pin and a pin, wherein the pin is arranged to move in the pin reception and relative to it.

The check valve arrangement is embodied in some exemplary embodiments to adopt or take exactly one or at least one operating position in addition to an initial position.

In some exemplary embodiments, the initial state is the first functional position, which serves for sterilizing, and the operating state is the second functional position showing a check function or check valve function.

In some exemplary embodiments, the check valve assembly may alternatively or in addition to the pin-pin-reception connection comprise a pin-pin-reception guide or guide system.

In particular exemplary embodiments of the check valve assembly, the pin-pin-reception connection is embodied such that the check valve assembly remains in an operating position after applying force on the pin-pin-reception connection and/or after an impression of path on the pin-pin-reception connection also after the force was released. This continuation describes the condition herein indicated as locked or latched state. An alternative term for this condition is "remanent activation" or "remanently activated"

In some exemplary embodiments, the check valve assembly comprises in the initial state a bypass by means of which the sterilization fluid may flow through the check valve assembly.

In particular exemplary embodiments, the check valve assembly comprises only in the initial state a bypass for the flow of the sterilization fluid, but not also in the operating state.

In certain exemplary embodiments, the check valve assembly comprises in the initial state a bypass that does not serve for the main flow of the working fluid, for the flow through of the sterilization fluid.

In some exemplary embodiments of the check valve assembly, the pin-reception of the pin-pin-reception connection is the bypass or it encompasses or forms, at least in part, the bypass.

In specific exemplary embodiments of the check valve assembly, the pin-reception is a clearance hole or a blind hole.

In certain exemplary embodiments of the check valve assembly, the pin-reception is a result of drilling; a result of insert molding in others.

In some exemplary embodiments of the check valve assembly, the pin-reception exclusively, or at least in a section of it, comprises a circular cross section.

In particular exemplary embodiments of the check valve assembly, the pin of the pin-pin-reception connection is of hollow interior and it encompasses or forms, at least in part, the bypass.

In certain exemplary embodiments of the check valve assembly, the pin of the pin-pin-reception connection is continuously or section wise hollow.

In some exemplary embodiments of the check valve assembly, the pin of the pin-pin-reception connection is open, at least partially, on one or on both of its front or end areas.

In particular exemplary embodiments of the check valve assembly, the pin of the pin-pin-reception connection comprises side openings, that is, those found in its shell surface.

In some exemplary embodiments of the check valve assembly, the pin-pin-reception connection is a pin-pin-reception combination.

In particular exemplary embodiments of the check valve assembly, the pin of the pin-pin-reception connection seals up, at least area wise, on its outer periphery against the valve body.

In some exemplary embodiments of the check valve assembly, the pin has in the area of its outer periphery "scope or clearance or play" for at least a part of the bypass flow.

In particular exemplary embodiments of the check valve assembly, the valve body comprises the pin as well as the pin-reception.

In certain exemplary embodiments, the check valve assembly in the operating state comprises a friction connection of the pin with at least one section of the pin-reception.

In specific exemplary embodiments, an outer diameter of the pin—in the area of its connection with (or its reception in) the pin-reception—is bigger, to an extent which may be denoted here as excess, than an inside diameter of the pin-reception which is required—in case this is desired- to achieve a friction closure between pin and pin-reception.

In some exemplary embodiments of the check valve assembly, the valve body comprises a first area with a pin-reception for the pin or for the pin-pin-reception connection, and a second area for sealing a flow path of the working fluid in the operating state, wherein the second area is more flexible or softer than the first area, or the first area is more rigid than the second area.

In particular exemplary embodiments of the check valve assembly, the valve body or a valve insert is made of hard resin or comprises resin.

In certain exemplary embodiments of the check valve assembly, the valve body or the valve insert is produced as a 2-component-injection-molded part.

In some of the exemplary embodiments of the check valve assembly, the pin-pin-reception connection is embodied so as to keep the check valve assembly in the operating state by friction or frictional closure and/or form closure.

In particular exemplary embodiments of the check valve assembly, the pin-pin-reception connection is embodied so as to keep the check valve assembly in the operating state solely by friction closure and/or form closure.

In some exemplary embodiments, the medical functional device is a blood cassette or blood tubing set, in particular for dialysis with at least one check valve assembly.

In particular exemplary embodiments of the medical functional device, the check valve assembly comprises a valve seat, and optionally a film for sealing the valve seat, the working fluid and/or the sterilization fluid against the surrounding.

In some exemplary embodiments of the medical functional device, the pin is connected to the valve seat or is part thereof. The pin-reception is movable or adjustable relative to the pin and it is part of the valve body.

In some exemplary embodiments of the medical functional device, the pin-reception is movable relative to the pin and it is part of the valve body while achieving a friction closure between pin and pin-reception.

In certain exemplary embodiments, the medical functional device is provided with at least two check valve assemblies which are arranged such that they are preferably transferable at the same time from the initial state into the operating state or may be activated as a check valve.

Some or all embodiments may comprise one or more of the advantages mentioned above or below.

In certain embodiments, a sealing lip is made of an elastomer. Due to the elasticity of the elastomer, the sealing lip is therefore advantageously used also as tolerance compensation, however, without significantly changing the opening pressure of the check valve assembly by an increase of a bias on the sealing lip.

In particular embodiments, areas of the check valve assembly which are made of elastomer advantageously serve for the tolerance compensation in an assembling procedure of the check valve assembly, in particular by pressing the valve body and the sealing lip into a cassette body. For example, upon pressing, a force may be applied to an elastomeric area that is connected to the sealing lip. This elastomeric area may also be connected to a valve body made of a hard resin, in particular a 2-component resin part (2-component injection molding part). Upon pressing, a force can be eventually and advantageously (preferably exclusively) applied to the elastomer, without damaging the valve body. This is a further advantageous tolerance compensation by means of the elastomer.

In some check valve assemblies, their activation, i.e. their check function may be advantageously maintained even after the removal of the medical functional device or the disposable embodied as a medical functional device by way of example. Thus, the leakage of liquid can be prevented also in case of the removal of the medical functional device, by the remanently (or permanently) activated check valve assembly. Hereby two hose clamps on the disposable and a required activity of the user for their actuation may be saved.

Furthermore, it requires no covering sleeve in the substitute connector (as described in International Patent Publication No. WO 2010/121819 A1 of the applicant of the invention for exemplary functional devices (there: a blood cassette)) and an associated working stroke of the machine to maintain the protection against contamination caused by the liquid leaking out of the medical functional device, for example, a blood cassette.

The check valve assemblies can advantageously ensure the necessary robustness against an early activation in the production prior to the sterilization.

Furthermore, the check valve assemblies, in the automatic production, may offer advantages in the safe sterilization and in the improvement of quality of the check valve functions. These include a secured continuance in the initial position, until completion of the gas sterilization, small and defined changes of features through the gas sterilization, in particular regarding the opening pressure, minimizing the changes of features in the built-in check valve assemblies by mechanical, thermal or irradiation-induced stress during storage and transport, which may affect the secure and accurate activation within the setting up procedure, avoidance of the previously tolerated projection or overlap of the film-side front area of the check valve assemblies over the film plane of the cassette (check valve assemblies cause local buckling in the film) to guarantee a safely producible film weld seam starting from a constant flat film placed on the cassette, a more tolerances-tolerant embodiment of the individual parts and their interaction both during assembly as well as in their interaction with the treatment machine while providing high reproducibility of the tightness of the opening pressure and the flow-pressure drop characteristics, and thereby secure function even in high volume production.

DETAILED DESCRIPTION

Figure 1A:
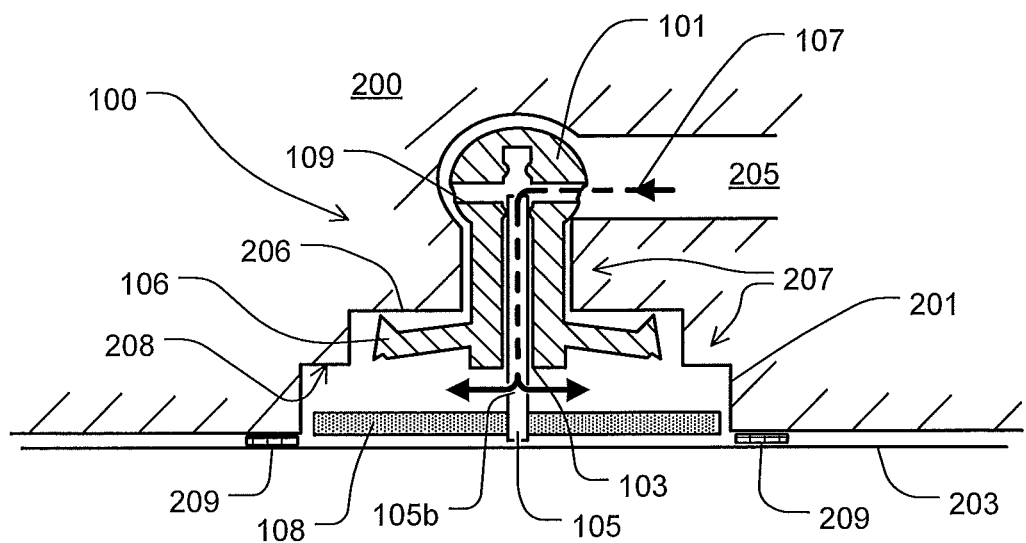
FIG. 1a shows a section of a check valve assembly according to a first embodiment in its initial state.

FIG. 1a shows a check valve assembly in a first embodiment as part of a medical functional device 200, here in the form of a blood cassette by way of example.

The blood cassette 200 comprises a cassette body 201, which is embodied as a hard part, and a film 203. It further comprises an inlet 205 for a working fluid (for example blood) as well as an outlet which is not shown because it is at a right angel to the drawing plane. The blood cassette 200 comprises a valve seat 207 in the area of its cassette body 201.

Fixations 209 keep the film 203 fixed to the cassette body 201. The fixation could be gluing connection, pressed connection, welded connection or the like.

The check valve assembly 100 is in the valve seat 207. This comprises a valve body 101 with a pin-reception 103 and a pin 105 inserted in the pin-reception 103. The pin-reception 103 and the pin 105 form a pin-reception-pin connection in which the pin 105 can move relative to the pin-reception 103 and is thereby guided by it.

The valve body 101 comprises furthermore a circumferentially closed sealing lip 106 which presses against a stop face 206 of the valve body 207 and causes the check valve effect of the check valve assembly 100 or hereto contributes to it.

In addition, the check valve assembly 100 or its valve body 101 comprises a circumferential switch plate 108 which is spaced here in the shown initial state from a stop face 208 for the switch plate 108. The switch plate 108 is connected to the pin 105 and serves for simple and tilt-safe application of force F on the pin 105.

Figure 1B:
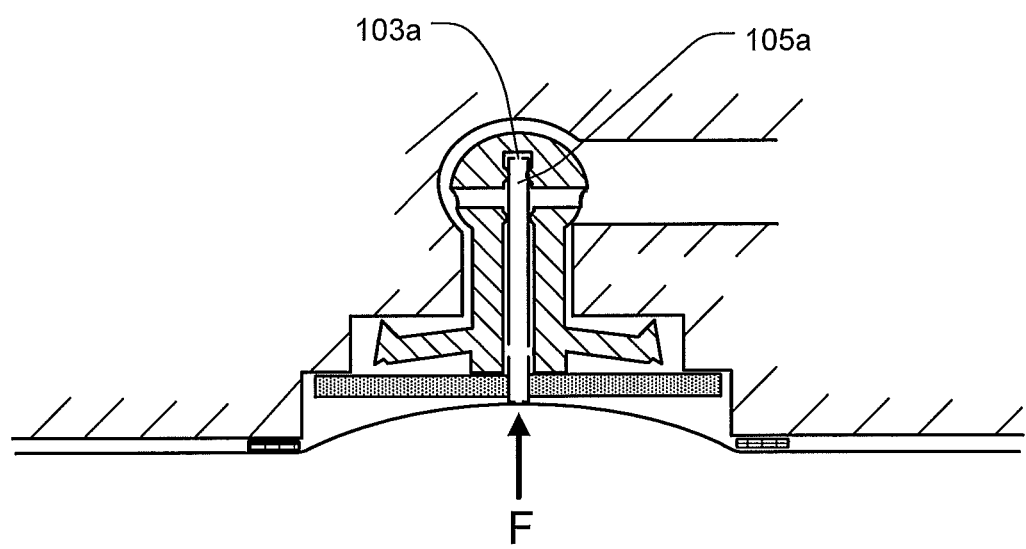
FIG. 1b shows the section of the check valve assembly of FIG. 1a in an operating state.

The check valve assembly 100 of FIGS. 1a and 1b is in FIG. 1a in the already closed state in which it, like a check valve, does not allow the sterilization agent to flow unlimitedly through its contained flow paths or the flow paths that are formed by it. However, it is not yet in a "locked state". A fluid, for instance a sterilization gas, flowing through the inlet 205 in direction of the valve body 101 can only or basically only enter through a bypass 107 in all sterilization relevant areas of the already closed check valve assembly 100 and spread throughout the valve body 101.

The fluid can continue to spread along an inlet opening 109 which is preferably orthogonal to the pin-reception 103. Alternatively or in addition, the fluid may, in certain exemplary embodiments, enter the long-stretched interior of the optionally hollow pin 105, and re-exit therefrom through non-illustrated opening in the side and/or front area of the pin 105. Alternatively or in addition, the bypass 107 is formed by the space between the distance area 208 and the switch plate 108.

FIG. 1b shows the check valve assembly 100 of FIG. 1a in an operating state in which the check valve assembly 100 acts as a check valve. The operating state, also referred to herein as the operating position is the active state, also referred to herein as a treatment state.

Figure 3:
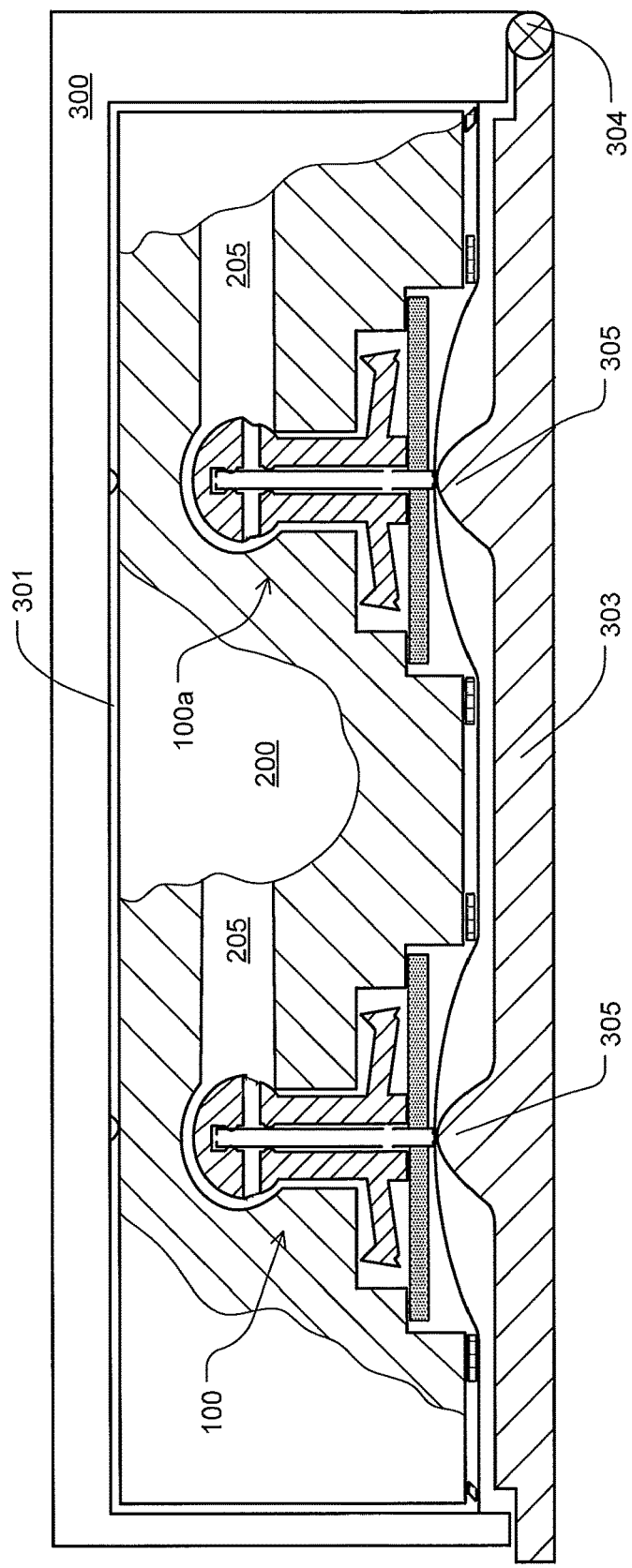

Due to a force F acting in the direction of the arrow, which is preferably being applied by a section, such as a door 303, of the treatment apparatus 300 shown only in FIG. 3, pressure was or is applied on the switch plate 108 and the pin 105 in a way that the pin 105 is pressed further into the valve body 101. This can lead to at least temporary dent in the film 203.

Through the application of the force F, the pin 105 was shifted so far along the pin-reception 103 towards the inside of the cassette body 200 so that the bypass 107 is now closed. A (working) fluid, for example blood, a medication or substitute, can flow through the check valve assembly 100 in the operating state shown here, in which the check valve is activated, only under correspondingly high pressure and only in the direction from the inlet 205 to the outlet, but not reversed.

The distance or space between the distance area 208 and switch plate 108 no longer exists. Both elements touch each other, which is a sign that the pin 105 was shifted sufficiently deep into the pin-reception 103.

As in the initial state of FIG. 1a the pin 103 is situated essentially in that section of the pin-reception 103, which, with respect to the illustration of FIG. 1b, lies below the inlet opening 109. Its end section 105a, in the operating state, is stuck in an end section 103a of the pin-reception which lies above the inlet opening 109 or can be recognized there.

The pin 103 still maintains the check valve position shown in FIG. 1b, even if the force F indicated or implied by an arrow subsides or is released. One can here speak of a locking of the pin 105 into the end section 103a of the pin-reception. A locking in the sense described herein exists or is available if the check valve assembly 100 upon release of the activation force F remains in the activated state without an effect or impact from outside of the medical functional device 200. It is thereby irrelevant whether the locking was achieved by form closure and/or friction closure. In the shown example, this is effected solely by a friction closure between pin-reception 103 and pin 105. Therewith, the friction closure can be present in areas below the inlet opening 109. The friction closure may alternatively or in addition be present in the end section 103a. In certain embodiments, friction closure exists both below and above the inlet opening 109. The friction closure being present below the inlet opening 109 can be determined or pre-set such that the pin 105, already during the setting up and with a film 200 that is not yet attached, cannot fall out of the pin-reception 103 anymore. This friction does not have to be set higher, and the lower it is the easier it is to move the pin 105 against the existing friction closure from the initial state to the operating state. In the operating state, the friction closure present in the end area 103a and 105a of pin-reception and pin, can compared hereto be higher. It is anyhow so high that the friction closure is as a whole sufficient in the operating state to ensure a lock of the pin 105, while in the operating position, also beyond termination of treatment and also in case of release of the force F, in order to keep the check valve assembly 100 in the activated locked state.

Alternatively or in addition to the herein described friction closure, by which the pin 105, after it has been moved by the force F, is stuck in the position shown in FIG. 1b in the pin-reception 103, which maintains the operating state; this position can be produced and maintained by a form closure. In this manner a snap-action connection, a barb system or the like may ensure that the pin 105 remains in its (operating) position.

As shown in FIGS. 1a and 1b, the inlet opening 109 connects the interior of the valve body 101 with its exterior by means of several openings, or at least by one opening. In FIG. 1a, two such exemplary openings are shown, which are arranged by way of example on the left and right edge of the valve body 101 and are in fluid contact via a horizontal connection in FIG. 1a. By providing several inlet openings 109, it is possible to advantageously dispense with a positional mark or with a structural coding for ensuring a correct installation of the mostly rotationally symmetrical designed valve body.

The check valve assembly 100 shown in FIGS. 1a and 1b is already closed in the position shown in FIG. 1a (i.e. the components relevant to the check-valve effect are already in position for achieving a check-valve effect).

The flow of sterilization medium is ensured by the bypass 107. However, also encompassed are check valve assemblies which in each unlatched (initial) state are still sufficiently permeable for the sterilization agent. Such embodiments do not require a bypass. An example of such an embodiment is shown in FIGS. 2a to 2c.

Figure 2A:
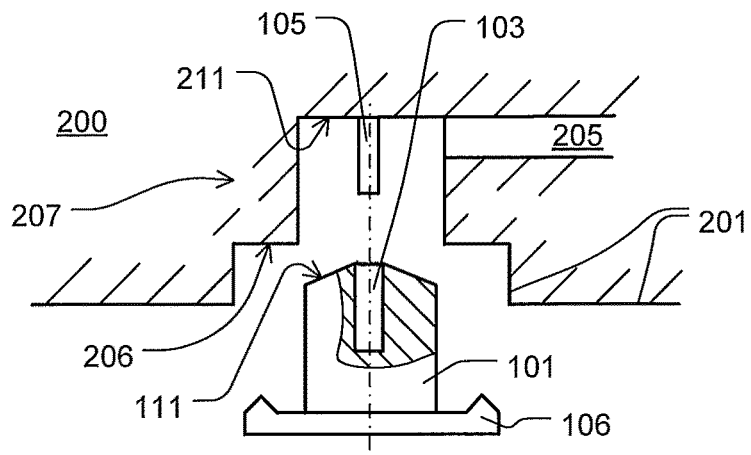
FIG. 2a shows the section of the check valve assembly according to a second embodiment in an exploded view.
Figure 2B:
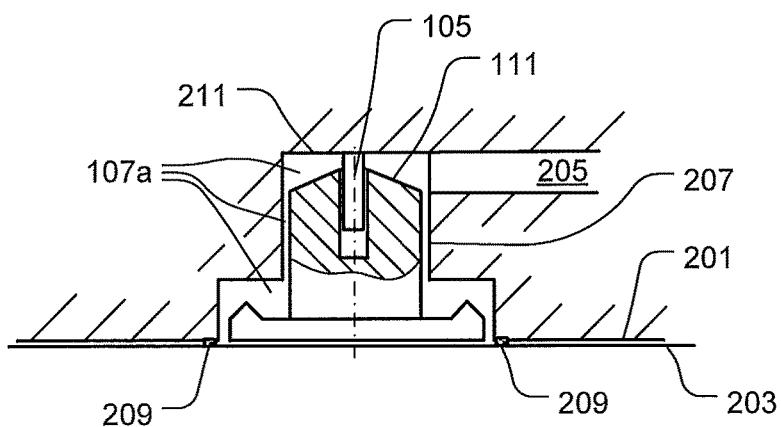
FIG. 2b shows the section of the check valve assembly of FIG. 2a in an initial state.

FIG. 2a shows a check valve assembly 100 in a second embodiment in an exploded view. The embodiment of FIG. 2a differs from that of FIGS. 1a and 1b, amongst others, in that the pin 105 is part of the valve seat 207, but not of the valve body 101. The pin-reception 103 is on the other hand, as also in FIGS. 1a and 1b, part of the valve body 101. The pin-reception 103, as in the first embodiment of FIG. 1a, is in an interior of the valve body and opens out or ends into a front area of the valve body. In the second embodiment shown here, the pin-reception 103 serves as a guiding and holding pin-reception, the pin 105 serves as a guiding and holding pin. The pin-reception 103 is embodied exemplarily as a blind hole or stud hole.

The embodiment of FIG. 2a differs further from that of FIGS. 1a and 1b in that it comprises no switch plate 108, and no bypass 107.

Figure 2C:
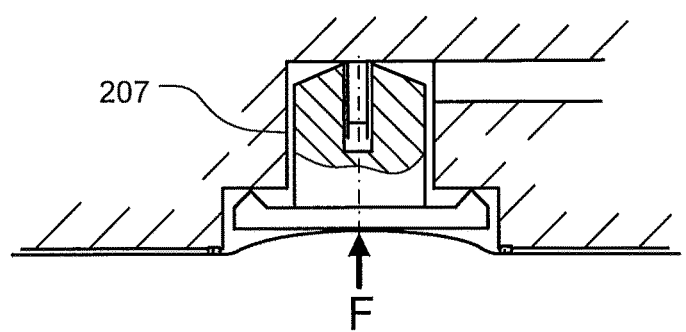
FIG. 2c shows the section of the check valve assembly of FIGS. 2a and 2b in an operating state and FIG. 3 shows in a schematically highly simplified manner a top view on a blood treatment apparatus 300.

With respect to FIG. 2a, the upper front area 111 of the valve body 101 is, in its interaction with the receiving area 211 of the valve seat 207 for the valve body 101, embodied such that these components when they get in contact with each other result in a seal as shown in FIG. 2c.

The valve body 101 is, here purely by way of example, made of resin, especially polycarbonate (abbreviated PC). The sealing lip 106, purely by way of example, is made of elastomer. The valve insert, consisting of valve body 101 and sealing lip 106 or comprising them, is thus produced as a 2-component part, preferably sprayed or casted (2-component injection molding part).

FIG. 2b shows the check valve assembly 100 of FIG. 2a in the initial state, the unlatched and—consequently—also the non-activated sterilization state. In this state, the check valve assembly 100 may have the flow through of gas or liquid for the purpose of sterilization—unhindered by a check valve function as this is not activated yet. Hereto, the free (flow) path 107a, which results from the fact that, always with respect to FIG. 2a, the upper front area 111 of the valve body 101 does not yet have any contact with the receiving area 211 of the valve seat 207 for the valve body 101, and these components due to lack of contact with each other, result in no seal. As a result of this, the fluid can flow also through a gap which results between the shell surface of the valve body 101 and the inner cylinder wall of the valve seat 207. From here, the fluid may further move past the not yet closed sealing lip 106, which in FIG. 2b, unlike in FIG. 2c, does not touch the stop surface 206 of the valve seat 207 and therethrough does not seal it. Of course, a flow in the direction opposite to the flow direction mentioned here is possible as well.

The film 203 is already applied to the cassette body 201 and is affixed by fixations 209 to the latter, for example glued, welded, etc.

FIG. 2c shows the check valve assembly of FIGS. 2a and 2b in the operating state, in which the valve body 101 due to the force F, again indicated by arrow, is or was (that is, was both activated or latched) connected with the valve seat 207 by the pin-pin-reception connection, so that the valve body 101 would not give up or lose its check valve function even after release of the above-mentioned force.

The free path 107a is closed in the position of the valve body 101 with respect to the valve seat 207 shown in FIG. 2b. Fluids can flow only with a correspondingly high pressure and in the predetermined direction through the check valve assembly 100. The check valve assembly 100 serves, therefore, in the activated state, for the operating state of a sealing of the medical functional device 200 even after it has been loosened or removed from the blood treatment apparatus or removed from it.

FIG. 3 shows in a schematically highly simplified manner, a plan view of a blood treatment apparatus 300 which comprises a receiving section 301 for receiving a medical functional device 200, here, a blood cassette. Furthermore, it comprises a movable limiting device 303, here, a door. The door shown in a cross-section is fastened by a hinge 304 to the blood treatment apparatus 300, and can be pivoted by it from the opened position non-shown in FIG. 3 in which the blood cassette 200 can be removed from the blood treatment apparatus 300 into the position shown here in which the receiving section 301 is closed.

The blood cassette 200 comprises in addition to the check valve assembly 100 already known from the preceding figures, a second check valve assembly 100a.

The limiting device 303 or door comprises two activation plungers 305. They are arranged so that to apply activation force, denoted above with F, at the same time, on either both valve bodies 101 or both pins 105 of the check valve assemblies 100 and 100a.

The number of check valve assemblies 100, 100a shown in FIG. 3 is purely exemplary. There may be more or less check valve assemblies provided.

The fixation of the limiting device 303 or door on the blood treatment apparatus 300 is also shown by way of example as a hinge connection. Any other mechanism by which one or more check valve assemblies, preferably automatically, preferably at the same time, can be activated can be used.

REFERENCE NUMERALS 100 check valve assembly
100a second check valve assembly
101 valve body
103 pin-reception
103a end section
105 pin
105a end section 106 sealing lip
107 bypass
107a free path
108 switch plate
109 inlet opening
111 front area of the valve body
200 medical functional device, blood cassette
201 cassette body
203 film
205 supply
206 stop face
207 valve body
208 stop face
209 fixations
211 receiving area
300 blood treatment apparatus
301 receiving section
303 movable limiting device, door
304 hinge
305 activation plunges

The invention claimed is:

1. A check valve assembly having a fluid inlet and a fluid outlet, the check valve assembly comprising:
a valve body at least partially defining a pin-reception; and
a pin configured to be at least partially disposed in the pin-reception,
the pin and the pin-reception configured such that the check valve assembly can be transferred from an initial state into an operating state by a force applied to the pin or the valve body,
the check valve assembly in the initial state being configured to allow fluid to flow in two flow directions through the check valve assembly via a bypass that is open through an interior of the pin and an interior of the valve body, and
when the check valve assembly is in the operating state:
(i) the bypass is closed to prevent fluid flow through the interior of the pin and the interior of the valve body, and
(ii) the check valve assembly allows fluid to flow through the check valve assembly in only one of the two flow directions.

2. The check valve assembly according to claim 1, wherein the pin-reception at least partially encompasses or forms the bypass.

3. The check valve assembly according to claim 1, wherein the pin is configured such that an outer periphery of the pin at least partially forms a seal against the valve body.

4. The check valve assembly according to claim 1, wherein the check valve assembly in the operating state comprises a friction-closure connection of the pin with at least a section of the pin-reception.

5. The check valve assembly according to claim 1, wherein the valve body comprises a first section with the pin-reception and a second section for sealing a flow path of a working fluid in the operating state, wherein the second section is more flexible than the first section.

6. The check valve assembly according to claim 1, wherein the valve body comprises resin.

7. The check valve assembly according to claim 1, wherein the valve body is a 2-component-injection-molded part.

8. The check valve assembly according to claim 1, wherein the pin and the pin-reception are configured to hold the check valve assembly in the operating state by at least one of a frictional closure and a form closure.

9. A medical functional device comprising:
a check valve assembly having a fluid inlet and a fluid outlet, the check valve assembly comprising:
a valve body at least partially defining a pin-reception; and
a pin configured to be at least partially disposed in the pin-reception,
the pin and the pin-reception configured such that the check valve assembly can be transferred from an initial state into an operating state by a force applied to the pin or the valve body,
the check valve assembly in the initial state being configured to allow fluid to flow in two flow directions through the check valve assembly via a bypass that is open through an interior of the pin and an interior of the valve body, and
when the check valve assembly is in the operating state:
(i) the bypass is closed to prevent fluid flow through the interior of the pin and the interior of the valve body, and
(ii) the check valve assembly allows fluid to flow through the check valve assembly in only one of the two flow directions.

10. The medical functional device according to claim 9, wherein the check valve assembly comprises a valve seat and a film.

11. The medical functional device according to claim 9, wherein the pin is connected to a valve seat or is part thereof, and wherein the pin-reception is movable relative to the pin and is part of the valve body.

12. The medical functional device according to claim 9, further comprising at least one second check valve assembly comprising a second pin, the at least one second check valve assembly configured to be transferred from an initial state into an operating state by a force applied to the second pin or the valve body, the at least one second check valve assembly in the initial state being configured to allow fluid to flow through the at least one second check valve assembly in two flow directions, and the at least one second check valve assembly in the operating state being configured to allow fluid to flow through the at least one check valve assembly in only one of the two flow directions, the check valve assemblies being configured to be transferred from their respective initial states to their respective operating states at the same time.

13. The medical functional device according to claim 9, wherein the medical functional device is a medical fluid cassette.

14. The medical functional device according to claim 13, wherein the medical fluid cassette is a blood cassette.

15. The check valve assembly according to claim 1, wherein the force applied to the pin or the valve body to transfer the check valve assembly from the initial state into the operating state locks the pin within the valve body.

16. The check valve assembly according to claim 1, wherein the valve body is disposed along a flow path through the check valve assembly between the fluid inlet and the fluid outlet.

17. The check valve assembly according to claim 1, wherein, when the check valve assembly is in the operating state, the check valve assembly allows fluid to flow through the check valve assembly over an exterior of the valve body.

* * * * *